United States Patent [19]

Marx

[11] 4,427,010
[45] Jan. 24, 1984

[54] METHOD AND MEANS FOR COOLING INJURED PARTS OR AREAS OF A HUMAN OR ANIMAL BODY

[76] Inventor: Günter H. Marx, Postfach 1224, Günter-Caracciola-Str. 10, D - 8035 Gauting, Fed. Rep. of Germany

[21] Appl. No.: 311,863

[22] Filed: Oct. 15, 1981

[30] Foreign Application Priority Data

Oct. 18, 1980 [DE] Fed. Rep. of Germany ....... 3039468

[51] Int. Cl.$^3$ ............................ A61F 7/00; F25D 5/00
[52] U.S. Cl. ..................................... 128/402; 128/399; 252/70; 62/4
[58] Field of Search ............... 128/399, 400, 402, 82.1; 62/4; 252/73, 70; 206/219

[56] References Cited

U.S. PATENT DOCUMENTS

| | | | |
|---|---|---|---|
| 3,149,943 | 9/1964 | Amador | 128/402 |
| 3,191,392 | 6/1965 | Donnelly | 62/4 |
| 3,542,032 | 3/1968 | Spencer, Jr. | 128/399 |
| 3,804,077 | 4/1974 | Williams | 62/4 |
| 3,885,403 | 5/1975 | Spencer | 128/399 |
| 4,081,256 | 3/1978 | Donnelly | 252/70 |
| 4,296,801 | 10/1981 | Guex et al. | 252/70 |

FOREIGN PATENT DOCUMENTS 2747664 5/1979 Fed. Rep. of Germany .
2949909 6/1981 Fed. Rep. of Germany .

*Primary Examiner*—Vincent Millin
*Assistant Examiner*—Harry Macey
*Attorney, Agent, or Firm*—Staas & Halsey

[57] ABSTRACT

In a method and means (cooling pack) for cooling injured parts or areas of a human or animal body, xylite ($C_5H_{12}O_5$) is used as the cold means. The xylite is dissolved in crystalline form in an aqueous or non-aqueous fluid and brought into direct or indirect contact with the part or area of the body to be cooled. The xylite may preferably be accommodated in a flexible container to which the solvent fluid can be supplied directly or from a container joined thereto.

3 Claims, 5 Drawing Figures

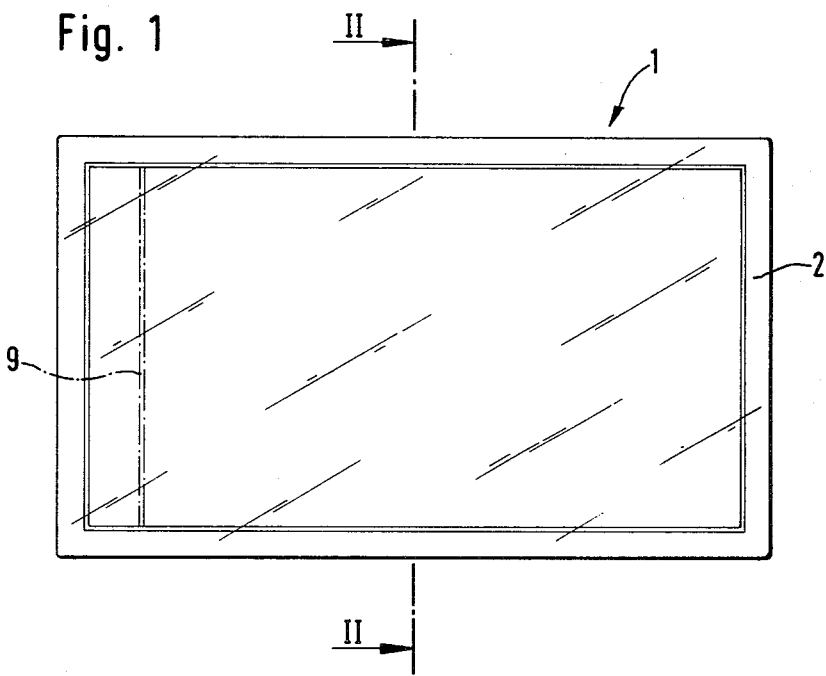
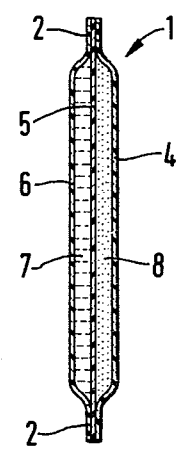
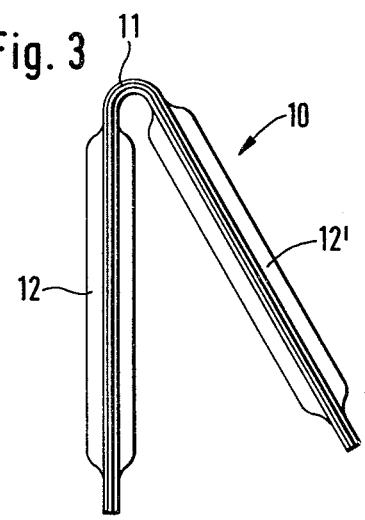

METHOD AND MEANS FOR COOLING INJURED PARTS OR AREAS OF A HUMAN OR ANIMAL BODY

BACKGROUND OF THE INVENTION

The invention is concerned with the use of xylite ($C_5H_{12}O_5$) for cooling injured parts or areas of a human or animal body, and a cooling pack in which the xylite is preserved in a particularly advantageous and ready-for-use form.

In medical practice, it is known and usual for injured parts and areas of a body to be cooled below the usual body temperature as quickly as possible after the injury has occurred, in order to slow down the metabolism in the cells in the region of the injury until treatment can be applied, and to eliminate reactions which are disadvantageous in regard to the heating process. Thus it is known for the region of the body affected by injury to be cooled with iced water in the case of sprains or ligament strains but also in the case of open wounds. Further, it is known for example for parts of a human body which have been cut off in an accident to be kept at the lowest possible temperature above freezing point until an operation (replantation) can be performed (see the applicants' German Offenlegungsschrift (laid-open application) No. 29 49 909).

In many cases, it is not possible effectively to cool the injured part of the body as quickly as possible after an injury has been suffered, due to the absence of a suitable cooling agent. This frequently applies even in regard to first-aid stations, ambulances and the like as ice for making iced water is available only when it can be constantly stored independently of the outside temperature. However, a serious problem is in particular the fact that, when dealing with open injuries and wounds, cooling cannot be considered when there is the fear of danger of infection or other damage caused by the cooling agent. The result of this is that open injuries, for example open fractures of limbs, cannot be cooled by means of water which possibly comes directly into contact with the wound.

There is therefore a need for a cooling means or agent for cooling injured parts or areas of a body to be held in preparation, at least in accident stations, ambulance vehicles and the like, which cooling means or agent can be stored unrestrictedly and irrespective of the outside temperature without separate cooling arrangements, and which does not give rise to any danger of infection or poisoning even in the event of its coming into direct contact with the injured or damaged tissue. In actual fact, so-called cooling packs are already known, which make use of the endothermic solution reaction of a salt in water for cooling therearound, for example ammonium nitrate which takes heat from the environment when it is dissolved in water and thereby causes a substantial drop in temperature. However, cooling agents of this kind are inconceivable for use in a medical connection for the above-discussed cooling purposes because, like ammonium nitrate, they are toxic and corrosive or caustic so that there must be a fear of considerable damage in the event of coming into direct contact with the wound. Even if it is theoretically possible for such cooling agents to be protected from direct contact with the parts or areas of the body to be cooled, by suitable packaging of the cooling agents, nonetheless in practice this danger cannot be totally excluded, for example due to the possibility of damage to the packaging, so that the resulting risk cannot be accepted.

A cooling pack is also already known wherein a flexible container comprising for example plastic foil is filled with a chemical, the melting point of which is in the temperature range which is to be assumed by a part of a body to be cooled (German Offenlegungsschrift (laid-open application) No. 23 05 504). The selection of the chemical involved is such that it is changed into the solid condition by the action thereon of a cold source and, when the cooling pack is used on an object, it absorbs its latent heat of fusion therefrom. This cooling pack maintains a constant cooling temperature until it reaches its melting point at which it is converted back into a liquid condition. This cooling pack also presupposes that there will be available a cooling source for changing it from the liquid into the solid aggregate condition, and the chemicals proposed for this purpose are of a kind which makes them unsuitable for use in particular on open wounds, for medical purposes.

SUMMARY OF THE INVENTION

An object of the present invention is to provide a cooling means or agent, capable of fulfilling the above-defined need.

To attain that and other objects, the invention proposes using xylite ($C_5H_{12}O_5$), by dissolving xylite in crystalline form in an aqueous or non-aqueous liquid and bringing the resulting solution into direct or indirect contact with the part or area of the body to be cooled.

Xylite (wood sugar) is a known sugar substitute which usually occurs in crystalline form at ambient temperature but which is also substantially stable (metastable) in amorphous form. The transition from the crystalline to the non-crystalline condition, for example in the dissolved form, occurs in the case of xylite with the absorption of heat, the energy required for breaking down the crystal lattice being taken from the environment, so that a fall in temperature occurs. This cooling effect is known per se but hitherto, to the applicant's knowledge, has not been put to use either generally or in the specific connection referred to herein.

The use of xylite as a cooling agent for cooling injured parts of a body has considerable advantages: xylite is completely non-toxic and harmless to the human body, both in the dissolved and in the crystalline state. It is even used for infusion purposes in artificial feeding. It can also be sterilised so that it also does not represent any danger from the point of view of carrying germs, and it is inert relative to virtually all known plastic materials used in the packaging industry. This means that it is possible for it to be used with a large number of conventional and in particular transparent or translucent packaging materials so that, in indirect cooling (cooling by heat transfer by way of an interposed container wall), the position of the cooling pack relative to the part or area of the body to be cooled can be monitored and controlled.

Another advantage is that it has an unrestricted service life and if required can be returned from the dissolved form back into the crystalline form. Even if regeneration is not involved, disposing of it after use does not give rise to any danger as it is completely non-toxic.

Xylite can be used in various manners, in accordance with the invention:

The simplest situation is for a given amount of fluid, for example water, to be added to a given amount of xylite in crystalline form so that the above-described cooling effect of the resulting solution occurs. If at the same time steps are taken for the solution which is contained for example in a flexible container to be brought into heat exchange contact with the part or area of the body to be cooled, that gives the desired cooling effect.

It is also possible however for fluid to be added continuously or stepwise and in metered amounts to a given amount of xylite, during the period of time for which the cooling action is to be produced, so that the amount of heat taken from the environment can be controlled in that way. In this manner, the cooling temperature can be controlled, and sub-cooling can be prevented from occurring.

Also in accordance with the invention is the preparation of a cooling pack which permits the use of xylite for the purposes of cooling, in ready-made form. The cooling pack is characterised by a flexible container which is desirably adapted in regard to its dimensions to the part or area of the body to be cooled and which comprises for example plastic or metal foil or film and which contains the xylite in crystalline form. By virtue of its flexibility, the container can be applied to and secured to the part of the body to be cooled by means of a bandage, compress or the like so that, after the xylite solution has been formed by the addition of fluid, the cooling effect is indirectly applied to the part or area of the body to be cooled. The xylite solution can be produced by fluid being added to the xylite by way of a feed aperture, the container either having the feed aperture from the outset or being designed to permit such a feed aperture to be produced, for example by a penetration position or a desired rupture position being provided on the container.

A particularly advantageous embodiment of the cooling pack provides that the container has a first chamber containing the xylite and a second chamber which contains a liquid and which is separated from the first chamber but can be brought into communication with the first chamber if required, for example at a desired rupture point. It will be appreciated that both the xylite and also the liquid are packaged in a sterile condition in the container so that the solution itself will also be sterile. The liquid can be passed into the quantity of xylite in the first chamber, or vice-versa, thereby to produce the solution, by deliberately rupturing the desired rupture point. The container can then be used directly as a cooling pack or cooling compress.

In this form also it is possible to provide for a metered feed of liquid to the xylite in the first chamber so that the total amount of heat which is to be drawn from the part or area of the body to be cooled can be drawn in such a way as to be distributed uniformly over the desired cooling period, thereby avoiding excessive cooling. This is a particularly important consideration when the outside temperatures, for example in winter, are already comparatively low in any case so that drawing the possible amount of heat from the body to be cooled within a short period of time could result in excessive cooling. In order to avoid this, the amount of liquid in the second chamber may be accommodated in a porous body, for example a sponge, so that either the amount of liquid can be passed to the xylite successively by applying a pressure to the porous body or sponge from time to time, or the liquid contained in the porous body diffuses into the xylite continuously in the course of time. In this respect, it is possible for the cooling pack to be of such a configuration that, after the communication has been made between the first and second chambers, the porous body is completely or partially pushed into the chamber containing the xylite so that the above-mentioned diffusion action in respect of the liquid into the xylite can take place over a large area.

Another simple design in regard to a cooling pack in accordance with the invention provides that a further container is contained within a container containing the xylite, which further container accommodates the fluid and can be destroyed by acting thereon from the outside.

Another possible way of setting a lower limit to the temperature of the solution and thus the temperature drop between the solution and the part or area to be cooled is for the xylite solution first to be produced using a first quantity of liquid, and then bringing a second quantity of liquid into heat-conductive communication with the xylite solution, whereby the temperature of the xylite solution can be moderated. This does not result in a loss of cooling effect as the amount of heat required for breaking down the crystal lattice structure is in any event taken from the solution and the additional liquid. The cooling effect results from the larger total amount—being larger than the previously colder xylite solution—and the temperature difference between the amount and the part to be cooled.

The cooling pack can also be of a shape which makes it particularly suitable for the purpose, for example bringing parts of a human body which have been severed in an accident to the operating table for the replantation operation, with minimum possible damage thereto and without detrimentally affecting the tissue in the region of the point at which the part of the body has been severed (see German Offenlegungsschrift No. 29 49 909 referred to above). In this form, the cooling pack represents a double-wall transportation container which has a first chamber which is accessible from the exterior, for receiving the part of the body which is to be transported, and a second chamber which is formed between the walls and which contains the xylite. In this case also it will be appreciated that the container comprises a flexible material, for example plastic or metal foil or film. The space formed by the double walls of the container can be constructed on the same principles as generally described hereinbefore in connection with the cooling pack, that is to say, it may have containing chambers which contain the xylite and the liquid for dissolving it, in such a way that they are initially separated from each other.

Water is primarily considered as the liquid for dissolving the xylite. However, it is also possible to envisage using other solvents which do not cause infection or poisoning of body tissue, for example alcohol. The liquid may also have added thereto a viscosity-increasing agent which obviously must also comply with the requirements in regard to medical acceptability. Methyl cellulose may be used for example for this purpose. By virtue of increasing the viscosity of the solution, it is easier for the cooling pack or compress to be held by means of a bandage or the like on the place which is actually to be cooled. The above-mentioned possibility of the solvent fluid being absorbed in a porous body such as a sponge also serves the same purpose.

BRIEF DESCRIPTION OF THE DRAWING

Simple embodiments of a cooling pack in accordance with the present invention are described in greater detail hereinafter with reference to the accompanying drawing in which:

FIG. 1 shows a plan view of the cooling pack,

FIG. 2 shows a view in section taken along line II—II in FIG. 1,

FIG. 3 shows an edge view of a modified embodiment of the cooling pack,

DESCRIPTION OF THE PREFERRED EMBODIMENTS

Figure 4:
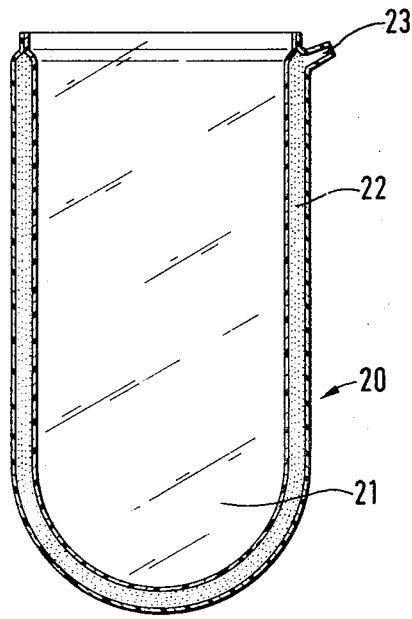
FIG. 4 shows a modified embodiment of the cooling pack in the form of a double-walled bag-like container.

Referring firstly to FIG. 1, shown therein is a cooling pack comprising a container 1 formed from transparent plastic film or foil. The container 1 is formed by welding along the edges, at a weld seam 2, of three superposed foils or films 4,5 and 6. The middle foil or film (see FIG. 2) forms a separating or partitioning wall between two chambers 7 and 8 which are formed by the outer films or foils 4 and 6, the first chamber 7 containing germ-free water and the second chamber 8 containing the xylite in crystalline form.

The middle film or foil 5 has a weakened portion 9 which extends over its width, as shown in broken lines in FIG. 1. The weakened portion 9 may be for example an impressed or imprinted portion. The middle film or foil 5 can be destroyed along the portion 9 either by a longitudinal pulling force applied in opposite directions to the two shorter sides of the cool pack, or by putting the contents of the pack under pressure, so that the two chambers 7 and 8 are brought into communication with each other. In this way, the water can pass from the chamber 7 into the xylite in the chamber 8, and dissolve the xylite. The cooling pack is then applied to the part or area of the body to be cooled, the transparent or at least translucent plastic foils 4, 5 and 6 making it possible to check that the cooling pack is properly arranged. The cooling pack is secured in position by means of a bandage. It is also possible however for securing means in the form of adhesive strips or the like to be disposed directly on the cooling pack itself.

The flat form of the cooling pack, as shown in the drawing, and the flexibility of the cool pack, due to the use of plastic films or foils comprising for example polyurethane, permit the cooling pack to be properly applied over a substantial area to the part of the body to be cooled.

In order to maintain the cooling effect for the maximum period of time possible, it is possible to envisage providing a heat-insulating layer on that side of the cooling pack which is remote from the part of the body to be cooled, the heat-insulating layer reducing heat exchange with the remainder of the surroundings.

FIG. 3 shows a modified embodiment of the cooling pack in the form of a flat bag 10 which corresponds in basic structural design to the embodiment shown in FIG. 1, that is to say, this embodiment also has the interior of the bag divided into two chambers by a separating film or foil. However, the outside walls of the bag are connected together by a weld seam 11 over their entire width, thereby providing two bag portions 12 and 12'. The two chambers in the bag portion 12 contain the xylite and the dissolving fluid, similarly to the embodiment shown in FIG. 1. On the other hand, the bag portion 12' only contains water (only one chamber is required in the bag portion 12'; it is only for manufacturing reasons that the separating film or foil also extends into the portion 12'). As can be seen from FIG. 3, the bag portion 12' which contains the water can be folded over about the seam 11 so that it is brought into heat-conducting areal contact with the bag portion 12. The purpose of this configuration is as follows:

If the ambient temperature is already comparatively low so that, when cooling a damaged part of a body with the cooling pack shown in FIG. 1, there is a danger of excessive cooling of the injured part of the body to a temperature below freezing point, then the additional amount of water in the bag portion 12' permits the temperature to be limited, in a downward direction, to a value which is at freezing point or above. For, if the ratio between the amounts of substances involved is properly determined, the heat of solution (180 J/g) which is taken off when the xylite dissolves is not sufficient to convert the entire amount of water (heat of fusion 334 J/g) into ice. However, as long as water is still present in liquid form, the temperature cannot fall below 0° C.

In such a situation, the cooling pack 10 is applied in a folded condition with the bag portion 12' against the part to be cooled, thereby reliably ensuring that excessive cooling cannot occur.

Instead of the construction shown in FIG. 3, it is obviously also possible for the third chamber to be arranged directly beside the other two chambers, by the interior of the bag being subdivided into three chambers by two separating film or foils. It will be appreciated that in that case it is not possible to use the cooling pack selectively with or without temperature limitation.

The arrangement may also be such that the container or bag for the 'moderating' water has a pocket or the like on its outside, for receiving a cooling element. Finally, it is of course also possible for the above-described temperature control effect to be achieved by joining or fitting together initially separate bags with the individual components involved.

Figure 5:
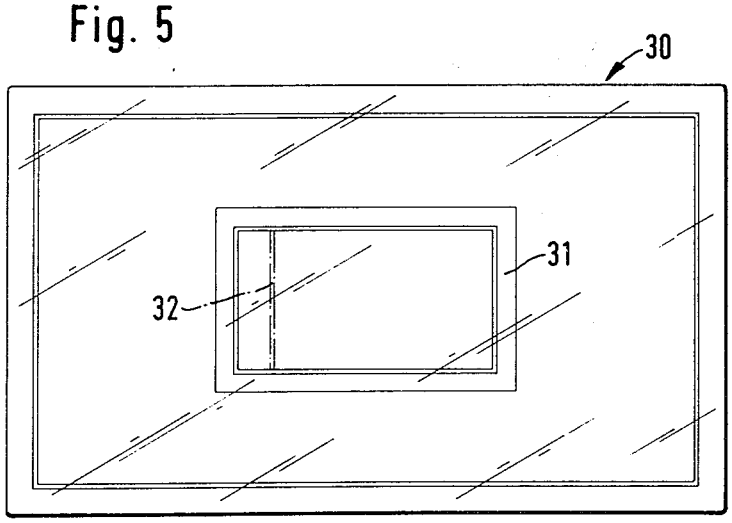
FIG. 5 shows another modified embodiment of the cooling pack.

Reference is now made to FIGS. 4 and 5 showing modified forms of the cooling pack according to the invention. In FIG. 4, the container for containing the xylite is in the form of a double-wall bag 20, into the interior 21 of which a part of a body to be cooled, for example a human foot, can be inserted, while a second space 22 is formed between the walls, for receiving the xylite. The space 22 is accessible by way of a closable opening 23 through which a solvent for the xylite, preferably water, can be introduced. Although this is not shown in greater detail, it may be possible for the opening leading to the first space 21 to be made of a closable configuration, for example by means of a draw cord.

In the embodiment shown in FIG. 5, the xylite is accommodated in a container in the form of a flat bag 30 which can correspond in respect of shape and material to the container 1 shown in FIG. 1. However, disposed in the bag 30 is a further bag 31 which can comprise the same material as the bag 30 and which contains the solvent for xylite. The bag 31 has a weakened portion or a desired rupture portion 32 which, in the event of the bag 31 being subjected to a pressure loading from outside the bag 30, for example by being squeezed in the hand, can be caused to burst so that the solvent contained therein flows into the surrounding xylite in the bag 30.

I claim:

1. A method of cooling an injured part of a human or animal body, wherein xylite ($C_5H_{12}O_5$) in crystalline form is dissolved in an aqueous or non-aqueous fluid and the resulting solution, while undergoing an endothermic reaction, is brought into direct or indirect contact with said part of the body.

2. A method as set forth in claim 1 wherein a viscosity-increasing agent is added to the fluid or said solution.

3. A method as set forth in claim 2 wherein methyl cellulose is added as the viscosity-increasing agent.

* * * * *